United States Patent [19]
Gray

[11] Patent Number: 5,985,868
[45] Date of Patent: Nov. 16, 1999

[54] METHODS AND COMPOSITIONS FOR TREATING ANDROGEN-DEPENDANT DISEASES USING OPTICALLY PURE R-(-) CASODEX

[75] Inventor: Nancy M. Gray, Cranbury, N.J.

[73] Assignee: Sepracor Inc., Marlborough, Mass.

[21] Appl. No.: 09/107,628

[22] Filed: Jun. 30, 1998

Related U.S. Application Data

[63] Continuation of application No. 08/662,043, Jun. 12, 1996, abandoned, which is a continuation of application No. 08/184,383, Jan. 21, 1994, abandoned.

[51] Int. Cl.$^6$ .......................... A61K 31/275; A61K 9/00; A61K 9/20
[52] U.S. Cl. .......................... 514/220; 424/400; 424/464; 514/859
[58] Field of Search .................................. 514/522, 859; 424/400, 464

[56] References Cited

PUBLICATIONS

Kennealey et al., "Use of the Nonsteroidal Anti-androgen Casodex in Advanced Prostatic Carcimona", Urologic Clinics of North America, V. 18, No. 1, pp. 99–110, 1991.

Furr, "Casodex (ICI 176,334)—A New, Pure, Peripherally--Selective Anti-Androgen:Preclinical Studies", Horm Res, V. 32 (suppl 1), pp. 69–76, 1989.

Cockshott et al., "The Pharmacokinetics of Casodex Enantiomers in Subjects With Impaired Liver Function", Br J Clin Pharmac, V. 36, pp. 339–343, 1993.

*Primary Examiner*—Shelley A. Dodson
*Assistant Examiner*—Marine Lamm
*Attorney, Agent, or Firm*—Heslin & Rothenberg, P.C.

[57] ABSTRACT

Methods and compositions are disclosed utilizing optically pure R-(−)-casodex for the treatment of androgen-dependent prostate cancer, while substantially reducing the concomitant liability of adverse effects associated with the racemic mixture of casodex. R-(−)-casodex is an antiandrogen and is therefore useful in the treatment of other conditions supported by androgen or caused by elevated androgen levels. Such conditions include benign prostatic hypertrophy or hyperplasia, acne and hirsutism.

16 Claims, No Drawings

METHODS AND COMPOSITIONS FOR TREATING ANDROGEN-DEPENDANT DISEASES USING OPTICALLY PURE R-(-) CASODEX

CROSS REFERENCE TO RELATED APPLICATIONS

This application is a continuation of earlier copending U.S. patent application, Ser. No. 08/662,043, filed Jun. 12, 1996, now abandoned, which is itself a continuation of U.S. patent application, Ser. No. 08/184,383, Jan. 21, 1994, now abandoned.

BACKGROUND OF THE INVENTION

This invention relates to novel compositions of matter containing optically pure R-(-)-casodex. These compositions possess potent activity in treating prostate cancer, benign prostatic hypertrophy or hyperplasia, acne and hirsutism and other diseases including those that would benefit from a selective androgen antagonist. Optically pure R-(-)-casodex provides this treatment while substantially reducing adverse effects including, but not limited to, gynecomastia, breast tenderness, hot flushes, nausea, vomiting, fatigue, diarrhea and bone pain, which are associated with the administration of the racemic mixture of casodex. Also disclosed are methods for treating the above described conditions in a human while substantially reducing the adverse effects that are associated with the racemic mixture of casodex by administering the R-(-) isomer of casodex to said human.

The active compound of these compositions and methods is an optical isomer of casodex. The preparation of racemic casodex is described in U.S. Pat. No. 4,636,505. Chemically, the active compound is the (-) isomer of N-[4-cyano-3-(trifluoromethyl) phenyl]-3-[(4-fluorophenyl)sulfonyl]-2-hydroxy-2-methylpropanamide, also known as 4'-cyano-3-[(4-fluorophenyl)sulfonyl]-2-hydroxy-2-methyl-3'-(trifluoromethyl)propionanilide, hereinafter referred to as casodex. The absolute stereochemistry of the (-) isomer is believed to be R as shown in formula I:

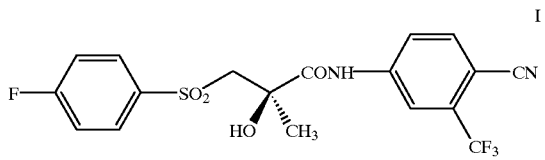

R-(-)-casodex, which is the subject of the present invention, is not presently commercially available. All of the clinical studies that have been reported have utilized the racemic mixture.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (-) are employed to designate the sign of rotation of plane-polarized light by the compound, with (-) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (-) lactic acid, and L-lactic acid is (+). For a given chemical structure, these chiral compounds exist as a pair of enantiomers which are identical except that they are non-superimposable mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

The chromatographic separation of a diastereomeric pair of R-camphanoyl esters of racemic casodex and their hydrolysis and oxidation to (+)-casodex and (-)-casodex on a milligram scale is described by Tucker and Chesterson, *J. Med. Chem.* 31, 885–887 (1988). The $ED_{50}$ of R-(-)-casodex in inhibiting androgen in rats was reported to be 0.5 mg/kg in vivo.

Racemic casodex is presently in clinical trials for use in prostate cancer. [See Kennealey and Furr, *Urol. Clin. North Am.* 18, 99–110 (1991), Mahler and Denis, *J. Steroid Biochem. Molec. Biol.* 37, 921–924 (1990); and Newling, *Eur. Urol.* 18 (Suppl), 18–21 (1990)]. The results of the preliminary clinical studies indicate that racemic casodex may be clinically useful in treating prostate cancer and other androgen-dependent diseases because of its antagonist activity at peripheral androgen receptors.

Androgens have been implicated in the progression of several diseases, including human prostate cancer, where they appear to provide the major hormonal support for cancer cells. It is generally accepted that antiandrogens can play an important role in the endocrine treatment strategy for patients with prostate cancer. Racemic casodex has been found to be a very selective antagonist at peripheral androgen receptors with little if any agonist component and no progestational or glucocorticoid activity.

In human volunteers doses of 10–50 mg p.o. per day resulted in a 50 to 60% reduction in prostatic acid phosphatase levels. Over half the patients receiving racemic casodex at 30 or 50 mg reported gynecomastia and breast tenderness, about 20% reported hot flushes, and less than 10% reported nausea and vomiting, bone pain, confusion, constipation, headache, diarrhea, dyspepsia, fatigue, dizziness or rash. Significant but mild elevations of serum testosterone, estradiol and LH were observed at all doses.

The average half life for racemic casodex, estimated from oral studies, was about 8 days. While clinical trials have so far been limited to prostate cancer, it is believed that as a result of its antiandrogen activity, racemic casodex may also be useful to treat benign prostatic hypertrophy or hyperplasia, acne and hirsutism and other androgen-dependent diseases.

Thus it would be particularly desirable to find a compound with the advantages of the racemic mixture of casodex which would not have the aforementioned disadvantages

SUMMARY OF THE INVENTION

It has now been discovered that the optically pure (-) isomer of casodex is an effective agent for treating androgen-dependent prostate cancer, benign prostatic hypertrophy or hyperplasia, acne, hirsutism and other diseases including those that would benefit from a selective antiandrogen. The optically pure (−) isomer of casodex provides this effective treatment while substantially reducing the adverse effects of racemic casodex including, but not limited to, gynecomastia, breast tenderness, hot flushes, nausea and vomiting, bone pain, confusion, constipation, headache, diarrhea, dyspepsia, fatigue, dizziness, rash and elevations of serum testosterone, estradiol and LH. The present invention also includes methods for treating the above described conditions in a human while substantially reducing the adverse effects that are associated with the racemic mixture of casodex by administering the optically pure (−) isomer.

DETAILED DESCRIPTION OF THE INVENTION

The present invention encompasses a method of treating prostate cancer, which comprises administering to a human in need of such therapy, an amount of R-(−)-casodex, substantially free of its (+) stereoisomer, said amount being sufficient to retard the growth of the cancer. The method substantially reduces the concomitant liability of adverse effects associated with the administration of the racemic compound.

The present invention also encompasses a composition for the treatment of a human afflicted with prostate cancer, which comprises a therapeutically effective amount of R-(−)-casodex, substantially free of its (+) stereoisomer, and a pharmaceutically acceptable carrier.

A further aspect of the present invention includes a method of treating a condition supported by androgen or caused by elevated androgen levels in a human, which comprises administering to a human in need of such therapy, an amount of R-(−)-casodex, substantially free of its (+) stereoisomer, sufficient to block a majority of peripheral androgen receptors. The method substantially reduces the concomitant liability of adverse effects associated with the administration of racemic casodex. Conditions that may be treated with an antiandrogen in humans may include, but are not limited to, benign prostatic hypertrophy or hyperplasia, acne and hirsutism.

In addition, the invention encompasses a composition for the treatment of a condition supported by androgen or contributed to by elevated androgen levels in a human which comprises a therapeutically effective amount of R-(−)-casodex, substantially free of its (+) stereoisomer, and a pharmaceutically acceptable carrier.

The racemic mixture of casodex (i.e., a 1:1 mixture of the two enantiomers) exhibits anticancer activity through its selective and potent antiandrogen activity, thus providing therapy and a reduction of symptoms in a variety of conditions and disorders related to the presence of androgen in disadvantageous amounts. However, this racemic mixture, while offering the expectation of efficacy, causes adverse effects. Utilizing the optically pure or substantially optically pure isomer of R-(−)-casodex results in enhanced efficacy, diminished adverse effects and, accordingly, an improved therapeutic index. It is therefore more desirable to use the (−) isomer of casodex than to administer the racemic mixture.

The term "adverse effects" includes, but is not limited to, gynecomastia, breast tenderness, hot flushes, nausea and vomiting, bone pain, confusion, constipation, headache, diarrhea, dyspepsia, fatigue, dizziness, rash and elevations of serum testosterone, estradiol and LH.

The term "substantially free of its (+) stereoisomer" as used herein means that the compositions contain at least 90% by weight of R-(−)-casodex and 10% by weight or less of (+) casodex In a more preferred embodiment the term "substantially free of the (+) isomer" means that the composition contains at least 99% by weight of R-(−)-casodex, and 1% or less of (+) casodex. In the most preferred embodiment, the term "substantially free of its (+) stereoisomer" as used herein means that the composition contains greater than 99% by weight of R-(−)-casodex. These percentages are based upon the total amount of casodex in the composition. The terms "substantially optically pure (−) isomer of casodex" or "substantially optically pure R-(−)-casodex" and "optically pure (−) isomer of casodex" and "optically pure R-(−)-casodex" are also encompassed by the above-described amounts.

The term "treating prostate cancer" as used herein means treating, alleviating or palliating such condition, suppressing the growth of cancerous tissue and thus providing increased survival time.

The term "treating a condition supported by androgen or contributed to by elevated levels of androgen" as used herein means treating, alleviating or palliating such disorders, thus providing relief from the symptoms of the aforementioned conditions or slowing the progression of the disease. Among such conditions are benign prostatic hypertrophy or hyperplasia, acne and hirsutism.

The term "therapeutically effective amount" refers to that dosage of R-(−)-casodex which is sufficient to suppress the growth of prostate cancer, reduce androgen levels, or block a majority of peripheral androgen receptors, but insufficient to cause the adverse effects associated with racemic casodex.

The chemical synthesis of the racemic mixture of casodex can be performed by the method described in U.S. Pat. No. 4,636,505 cited above. The (−) isomer of casodex may be obtained by resolution of the enantiomers of casodex or of precursors thereto using fractional crystallization or chromatography of diastereomeric esters of chiral acids. Other standard methods of resolution known to those skilled in the art including, but not limited to, simple crystallization and chromatographic resolution, can also be used. (See for example, E. L. Eliel, *Stereochemistry of Carbon Compounds,* McGraw Hill (1962) and [Wilen and Lochmuller, "Tables of Resolving Agents", Journal of Chromatography 113, 283–302 (1975)]. In addition, the carboxylic acid precursor, 3-(4-fluorophenyl)-2-hydroxy-2-methylpropanoic acid, may be resolved by fractional crystallization of diastereomeric salts with chiral amines.

The magnitude of a prophylactic or therapeutic dose of R-(−)-casodex in the acute or chronic management of disease will vary with the severity and nature of the condition to be treated and the route of administration. The dose and perhaps the dose frequency will also vary according to the age, body weight and response of the individual patient. In general, the total daily dose range for R-(−)-casodex for the conditions described herein is from about 10 mg to about 50 mg. Preferably a daily dose range should be about 20 mg to about 40 mg, while the most preferable daily dose should be about 30 mg. In managing the patient, the therapy should be initiated at a lower dose, perhaps at about 10 mg to about 20 mg, and increased up to about 40 mg or higher depending on the patient's global response. It is further recommended that patients over 65 years and those with impaired renal or hepatic function initially receive low doses and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "an amount sufficient to suppress cancer but insufficient to cause said adverse effects" and "an amount sufficient to block a majority of peripheral androgen receptors but insufficient to cause said adverse effects" are encompassed by the above-described dosage amounts and dose frequency schedule.

Any suitable route of administration may be employed for providing the patient with an effective dosage of R-(-)-casodex. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise R-(-)-casodex as the active ingredient, and may also contain a pharmaceutically acceptable carrier, and optionally, other therapeutic ingredients.

The compositions of the present invention include suspensions, solutions, elixirs, or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent the most advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet contains from about 10 mg to about 50 mg of the active ingredient, and each cachet or capsule contains from about 10 mg to about 50 mg of the active ingredient. Most preferably, the tablet, cachet or capsule contains either one of two dosages, about 20 mg or about 30 mg of R-(-)-casodex for oral administration.

The invention is further defined by reference to the following examples describing in detail the preparation of the compositions of the present invention, as well as their utility. It will be apparent to those skilled in the art that many modifications, both to materials and methods, may be practiced without departing from the purpose and interest of this invention.

The relative activity, potency and specificity of optically pure casodex and racemic casodex as an antiandrogen can be determined by pharmacological studies in vitro and in vivo according to the methods of Christiansen et al. *J. Med. Chem.* 33, 2094–2100 (1990).

Rat Prostate Androgen Receptor Competition Assay. Cytosol is prepared with ventral prostates from castrated adult rats weighing approximately 250 g. Tissues are homogenized in TMDG buffer (10 mM TRIS, 20 mM molybdate, 2.0 nM dithiothreitol, 10% glycerol, pH=7.4) and centrifuged at the equivalent of 105000 g for 1 h. Aliquots of the supernatant is (cytosol) are incubated with a labelled androgen-receptor ligand such as [$^3$H]-R1881 (methyltrienolone, 5 nM final concentration) in either the absence or presence of increasing concentrations $10^{-9-10-5}$M) of unlabelled (cold) ligand, reference, or test compounds for 1 h or overnight (approximately 18 h) at 4° C. Because [$^3$H]-R1881 binds weakly to progesterone and glucocorticoid receptors (approximately 5% at 5 nm), cytosols may be pretreated with 1 $\mu$M triamcinolone acetonide to block these interactions. After the 1- or 18-h incubation period, a suspension of dextran coated charcoal (1% charcoal, 0.05% dextran T-70) is added to the ligand/cytosol mixture and incubated for 5 min. The charcoal-bound [$^3$H]-R1881, i.e. non-protein bound, is removed by centrifugation, and the supernatant (protein-bound [$^3$H]-R1881) is counted. Relative binding affinities (RBA; used to quantify receptor binding competition) are calculated as the ratio of the concentration required to inhibit [$^3$H]-R1881 specific binding by 50% (with R1881 arbitrarily set at 100).

Androgenic/Antiandrogenic Activity in Castrated Immature Rats. Weanling Sprague-Dawley male rats are castrated and, beginning 1 week later, grouped by body weight and medicated orally with the test compound in the absence or presence of testosterone propionate (0.8 mg/kg/sc) for 10 consecutive days. The day following the last medication, the rats are weighed and sacrificed. The ventral prostate of each rat is removed, blotted and weighed. Antiandrogenic activity is characterized by a graphically determined $ED_{50}$ defined as the dose required to inhibit testosterone propionate stimulated prostate weight gain by 50%.

The tests provide an estimate of relative activity and potency.

Emesis in Ferrets. Experiments are performed on adult, male ferrets. The animals are first adapted to wearing a nylon jacket connected to a stainless-steel cable, which in turn is attached to a brass swivel at the cage top, After habituation to the tether-harness, each animal receives a surgically implanted catheter in its right jugular vein. The catheter is flushed daily with heparinized sodium chloride. The drug studies are conducted 1 week after the surgical procedure. Tethered animals are individually housed.

Eight to eleven animals are used to evaluate each dose of each test compound. Individual animals are weighed weekly and randomly given, at greater than 48 hour intervals, a single i.v. or p.o. dose of racemic casodex, (+)-casodex or (−)-casodex. At least three dose levels of each test compound are evaluated.

Individual animals are observed for 30 minutes following administration of the test substance. The frequency of, and latency to all expulsions, retches and defecations are recorded. Data obtained from dose-response curves are tested for statistical significance by chi-square analysis. $ED_{50}$ values are determined for each compound. The test provides an estimate of relative liability to a common side effect.

EXAMPLES

Example 1

ORAL FORMULATION

Capsules:

| Formula | Quantity per capsule in mg | | |
|---|---|---|---|
| | A | B | C |
| R-(−)-casodex | 10 | 30 | 50 |
| Lactose | 204 | 184 | 164 |
| Cornstarch | 35 | 35 | 35 |
| Magnesium Stearate | 1.0 | 1.0 | 1.0 |
| Fill Weight | 250 | 250 | 250 |

The R-(−)-casodex, lactose and cornstarch are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit.

Example 2

ORAL FORMULATION

Tablets:

| Formula | Quantity per tablet in mg | | |
|---|---|---|---|
| | A | B | C |
| R-(−)-casodex | 10 | 30 | 50 |
| Lactose | 149 | 129 | 109 |
| Cornstarch | 30 | 30 | 30 |
| Water (per thousand Tablets)* | 150 mL | 150 mL | 150 mL |
| Cornstarch | 60 | 60 | 60 |
| Magnesium Stearate | 1.0 | 1.0 | 1.0 |
| Compression Weight | 250 | 250 | 250 |

*The water evaporates during manufacture

The R-(−)-casodex is blended with the lactose until a uniform blend is formed. The smaller quantity of cornstarch is blended with the water to form the resulting corn starch paste. This is then mixed with the uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are dried in a suitable drying oven until the desired moisture content is obtained. The dried granules are then milled through a suitable milling machine, magnesium stearate is blended in, and the resulting mixture is compressed into tablets of the desired shape, thickness, hardness and disintegration. Tablets of other strengths may be prepared by altering the ratio of active ingredient to the excipients or to the final weight of the tablet.

What is claimed is:

1. A method of treating prostate cancer in a human which comprises administering to said human a therapeutically effective amount of R-(−) -[CASODEX] N-[4-cyano-3-(trifluoromethyl)phenyl]-3- [(4-fluorophenyl) sulfonyl]-2hydroxy-2-methylpropanamide,methylpropanamide, -(+) containing less than 10% by weight of S-(+)-[CASODEX] N-[4-cyano-3-(trifluoromethyl)phenyl]-3-[(4-fluorophenyl) sulfonyl]-2hydroxy-2-methylpropanamide.

2. The method of claim 1 wherein R-(−)[CASODEX]-N-[4-cyano-3-(trifluoromethyl) phenyl]-3-[(4-fluorophenyl) sulfonyl]-2-hydroxyl-2-methylpropanamide is administered by parenteral, transdermal, or oral administration.

3. The method of claim 2 wherein the amount of R-(−) [CASODEX]-N-[4-cyano-3-(trifluoromethyl)phenyl]-3-[(4-fluorophenyl)sulfonyl]-2-hydroxy-2methylpropanamide administered is from about 10 mg to about 50 mg per day.

4. The method of claim 3 wherein the amount administered is from about 20 mg to about 40 mg per day.

5. The method of claim 4 wherein the amount administered is about 30 mg per day.

6. The method of claim 1 wherein the amount of said R-(−)-[CASODEX]-N-[4-cyano-3-(trifluoromethyl) phenyl]-3-[(4-fluorophenyl) sulfonyl]-2-hydroxy-2-methylpropanamide is administered together with a pharmaceutically acceptable carrier.

7. A pharmaceutical composition which comprises a therapeutically effective amount of R-(−)[CASODEX]-N-[4-cyano-3-(trifluoromethyl)phenyl]-3-[(4-fluorophenyl) sulfonyl]-2-hydroxy-2-methylpropanamide containing less than 10% by weight of S-(+)- [CASODEX ] N-[4-cyano-3-(trifluoromethyl)phenyl-3-[(4-fluorophenyl)sulfonyl]-2-hydroxy-2-methylpropanamide, and a pharmaceutically acceptable carrier.

8. The composition according to claim 7 adapted for oral administration.

9. The composition according to claim 7 adapted for parenteral delivery.

10. A method of treating a condition supported by androgen or caused by elevated androgen levels in a human which comprises administering to said human a therapeutically effective amount of R-(−)- [CASODEX ] N-[4-cyano-3-(trifluoromethyl) phenyl]-3-[(4-fluorophenyl)sulfonyl]-2-hydroxy-2-methylpropanamide, containing less than 10% by weight of S-(+)- [CASODEX ] N-[4-cyano-3-(trifluoromethyl) phenyl]3-[(4-fluorophenyl)sulfonyl]-2-hydroxy-2-2-methylpropanamide.

11. The method according to claim 10 wherein said condition is chosen from the group consisting of benign prostatic hypertrophy or hyperplasia, acne and hirsutism.

12. The method of claim 10 wherein R-(−)- [CASODEX ] N-4-cyano-3-(trifluoromethyl) phenyl]-3-[(4-fluorophenyl)sulfonyl]-2-hydroxy-2-methylpropanamide is administered by parenteral, transdermal, or oral administration.

13. The method of claim 12 wherein the amount of R-(−)- [CASODEX ] N-[4-cyano-3-(trifluoromethyl)phenyl]-3-[4-fluorophenyl)sulfonyl]-2-hydroxy-2-methylpropanamide administered is from about 10 mg to about 50 mg per day.

14. The method of claim 13 wherein the amount administered is from about 20 mg to about 40 mg per day.

15. The method of claim 14 wherein the amount administered is about 30 mg per day.

16. The method of claim 11 wherein the amount of said R-(−)-[CASODEX ] N-[4-cyano-3-(trifluoromethyl) phenyl]-3-[4-fluorophenyl)sulfonyl]-2 hydroxy-2-methylpropanamide is administered together with a pharmaceutically acceptable carrier.

* * * * *

UNITED STATES PATENT AND TRADEMARK OFFICE
CERTIFICATE OF CORRECTION

PATENT NO. : 5,985,868

DATED : November 16, 1999

INVENTOR(S) : Nancy M. Gray

Page 1 of 2

It is certified that error appears in the above-identified patent and that said Letters Patent is hereby corrected as shown below:

ON THE TITLE PAGE:

Item [54], line two of the Title, delete "ANDROGEN-DEPENDANT" and replace with --ANDROGEN-DEPENDENT--.

Col. 1, line 2, delete "ANDROGEN-DEPENDANT" and replace with --ANDROGEN-DEPENDENT--.

Col. 8, Claim 1, line 4, delete "[CASODEX]".
Col. 8, Claim 1, line 6, delete "methylpropanamide, -(+)".
Col. 8, Claim 1, line 7, delete "[CASODEX]".
Col. 8, Claim 2, line 10, delete "[CASODEX]".
Col. 8, Claim 3, line 15, delete "[CASODEX]".
Col. 8, Claim 6, line 22, delete "[CASODEX]".
Col. 8, Claim 7, line 27, delete "[CASODEX]".
Col. 8, Claim 7, line 30, delete "[CASODEX]".
Col. 8, Claim 7, line 31, delete "(trifluoromethyl)phenyl-3-" and replace with --(trifluoromethyl)phenyl]-3- --.
Col. 8, Claim 10, line 40, delete "[CASODEX]".
Col. 8, Claim 10, line 43, delete "[CASODEX]".

UNITED STATES PATENT AND TRADEMARK OFFICE
CERTIFICATE OF CORRECTION

PATENT NO. : 5,985,868
DATED : November 16, 1999
INVENTOR(S) : Nancy M. Gray

It is certified that error appears in the above-identified patent and that said Letters Patent is hereby corrected as shown below:

Col. 8, Claim 10, line 45, delete "hydroxy-2-2-methylpropanamide" and replace with
--hydroxy-2-methylpropanamide--.
Col. 8, Claim 12, line 49, delete "[CASODEX".
Col. 8, Claim 12, line 50, delete "]", first instance.
Col. 8, Claim 13, line 55, delete "[CASODEX] ".
Col. 8, Claim 16, line 62, delete "claim 11" and replace with --claim 10--.
Col. 8, Claim 16, line 62, delete "[CASODEX ]".

Signed and Sealed this

Fifth Day of September, 2000

*Attest:*

*Attesting Officer*

Q. TODD DICKINSON

*Director of Patents and Trademarks*